United States Patent [19]
Richalley et al.

[11] Patent Number: 5,004,548
[45] Date of Patent: Apr. 2, 1991

[54] METHOD AND APPARATUS FOR RINSING AND PRIMING AN EXCHANGER

[75] Inventors: Gerard Richalley, Lyons; Jacques Burtin, Feyzin, both of France

[73] Assignee: Hospal Industrie, Cedex, France

[21] Appl. No.: 282,245

[22] Filed: Dec. 9, 1988

[30] Foreign Application Priority Data

Dec. 11, 1987 [FR] France .................. 87 17608

[51] Int. Cl.$^5$ .................. B01D 61/24; B01D 63/00
[52] U.S. Cl. .................. 210/646; 210/97; 210/321.72; 210/741; 210/777; 604/5
[58] Field of Search .................. 210/644, 645, 646, 741, 210/140, 777, 321.72–321.81, 97; 604/4–6; 427/245

[56] References Cited

U.S. PATENT DOCUMENTS 4,209,402 6/1980 Gentles .................. 210/140
4,588,407 5/1986 Isono et al. .................. 210/321.8

FOREIGN PATENT DOCUMENTS

2566273 1/1986 France .
PCT/US85/-
00124 1/1985 PCT Int'l Appl. .

Primary Examiner—W. Gary Jones
Attorney, Agent, or Firm—Finnegan, Henderson, Farabow, Garrett & Dunner

[57] ABSTRACT

A method and apparatus for rinsing and priming an exchanger divided into first and second compartments by a semi-permeable membrane, the first compartment intended for circulating blood to be treated and the second compartment intended for circulating a purifying liquid comprising the steps of circulating a sterile solution through the second compartment and depositing a protein film on at least one side of the membrane. The apparatus includes means for circulating a sterile solution through the second compartment, and means for depositing a protein film on at least one side of the membrane.

20 Claims, 8 Drawing Sheets

METHOD AND APPARATUS FOR RINSING AND PRIMING AN EXCHANGER

BACKGROUND OF THE INVENTION

1. Field of the Invention

The present invention relates to a method and apparatus for rinsing and priming an exchanger having two compartments separated by a semipermeable membrane. The first compartment is intended for the extracorporeal circulation of blood to be treated, and the second compartment is adapted to be connected to a dialysis liquid circuit.

2. Description of The Prior Art

Even though devices for the extracorporeal treatment of blood are carefully manufactured and are sterilized during the final stage of the manufacturing process, it is necessary to thoroughly rinse the exchangers before they are used. The purpose of rinsing is to eliminate possible manufacturing and sterilization residues which could lead to undesirable reactions (such as hypersensitivity reactions) if they were to pass into a patient's blood.

During the rinsing stage, sterile physiological liquid is usually circulated from a storage bag into the first compartment (blood compartment) of the hemodialyzer. In addition, liquid produced by a dialysis liquid generator, generally integrated with the dialysis monitor, circulates through the second compartment (dialysis compartment).

The sterile liquid intended for rinsing the blood compartment is generally circulated by means of a pump usually used for the circulation of the blood to be treated.

In order to ensure effective rinsing of the blood compartment, French Patent Application No. 2,566,273 proposes a washing method wherein a predetermined quantity of physiological saline solution, such as an aqueous solution of 0.9% sodium chloride, is circulated in the blood compartment and then immediately evacuated. Next, fresh physiological saline solution is circulated in the blood compartment. Finally, fresh physiological saline solution from a second source is circulated through the blood compartment.

Although the rinsing method described above has the advantage of efficiently eliminating possible residue in the blood compartment of the hemodialyzer, it nevertheless causes considerable inconvenience to the hospital staff charged with the preparation of a hemodialysis session.

Another problem inherent in the prior art method is that dialysis liquid used for rinsing the dialysate compartment may become contaminated. It is possible for substances such as bacterial derivatives to diffuse through the semipermeable membrane towards the blood compartment.

In addition, when the blood compartment is connected to the source of the blood to be treated, it is very difficult to control the pressures exerted inside each of the compartments of the hemodialyzer and to prevent substances which may be present in the dialysis liquid from passing through the membrane. The more permeable the membrane, the greater the problem.

Hypersensitive reactions caused by contaminated blood may occur during the first few minutes of the hemodialysis session and require the physician to interrupt the session immediately.

In order to improve the bacteriological quality of dialysis liquid, it has been proposed to filter the liquid before use. This requires the use of filters that increases the cost and maintenance operations to the dialysis liquid generator. In addition, the efficiency of these systems has been mediocre. Another problem with the filtration method is that there are bacterial derivatives capable of producing a biological effect whose size is so small that it is difficult to retain them by filtration. The prior art systems require in-line means for verifying filtration efficiency, as well as a safety device that prevents the use of dialysis liquid that has been inadequately filtered.

Accordingly, it is an object of the present invention to provide a method and apparatus for rinsing and priming an exchanger which does not have the drawbacks of the prior art and effectively eliminates manufacturing and sterilization residues.

An additional object of the present invention is to provide a method and apparatus for rinsing and priming of an exchanger to overcome the contamination caused by the dialysis liquid generator.

Another object of the present invention is to provide a simple and fast method and an apparatus for rinsing and priming a hemodialyzer.

Another object of the present invention is to provide a method and an apparatus for rinsing and priming a hemodialyzer that effectively rinses the hemodialyzer to prevent hypersensitivity reactions from occurring at the beginning of the treatment session.

A further object of the present invention is to provide an inexpensive method and apparatus for rinsing and priming an exchanger.

In addition, an object of the present invention is to provide a method and apparatus which is particularly suitable for an exchanger fitted with a membrane having high water permeability.

Additionally, an object of the present invention is to provide a method and a device for rinsing and priming an exchanger that does not require the use of a dialysis liquid generator.

Additional objects and advantages are set forth in part in the description which follows, and in part will be obvious from the description, or may be learned by practice of the invention. The objects and advantages of the invention may be realized and attained by means of the instrumentalities and combinations particularly pointed out in the appended claims.

SUMMARY OF THE INVENTION

In accordance with the purposes of the invention as embodied and broadly described herein, there is provided a method for rinsing and priming an exchanger divided into first and second compartments by a semipermeable membrane, the first compartment intended for circulating blood to be treated and the second compartment intended for circulating a purifying liquid. The method comprises the steps of circulating a sterile solution through the second compartment, and depositing a protein film on at least one side of the semi-permeable membrane.

BRIEF DESCRIPTION OF THE DRAWINGS

The accompanying drawings, which are incorporated in and constitute a part of the specification, illustrate preferred embodiments of the invention wherein like reference numerals refer to like elements throughout, and, together with the description serve to explain the principles of the invention.

DETAILED DESCRIPTION OF THE PREFERRED EMBODIMENTS

Figure 1:
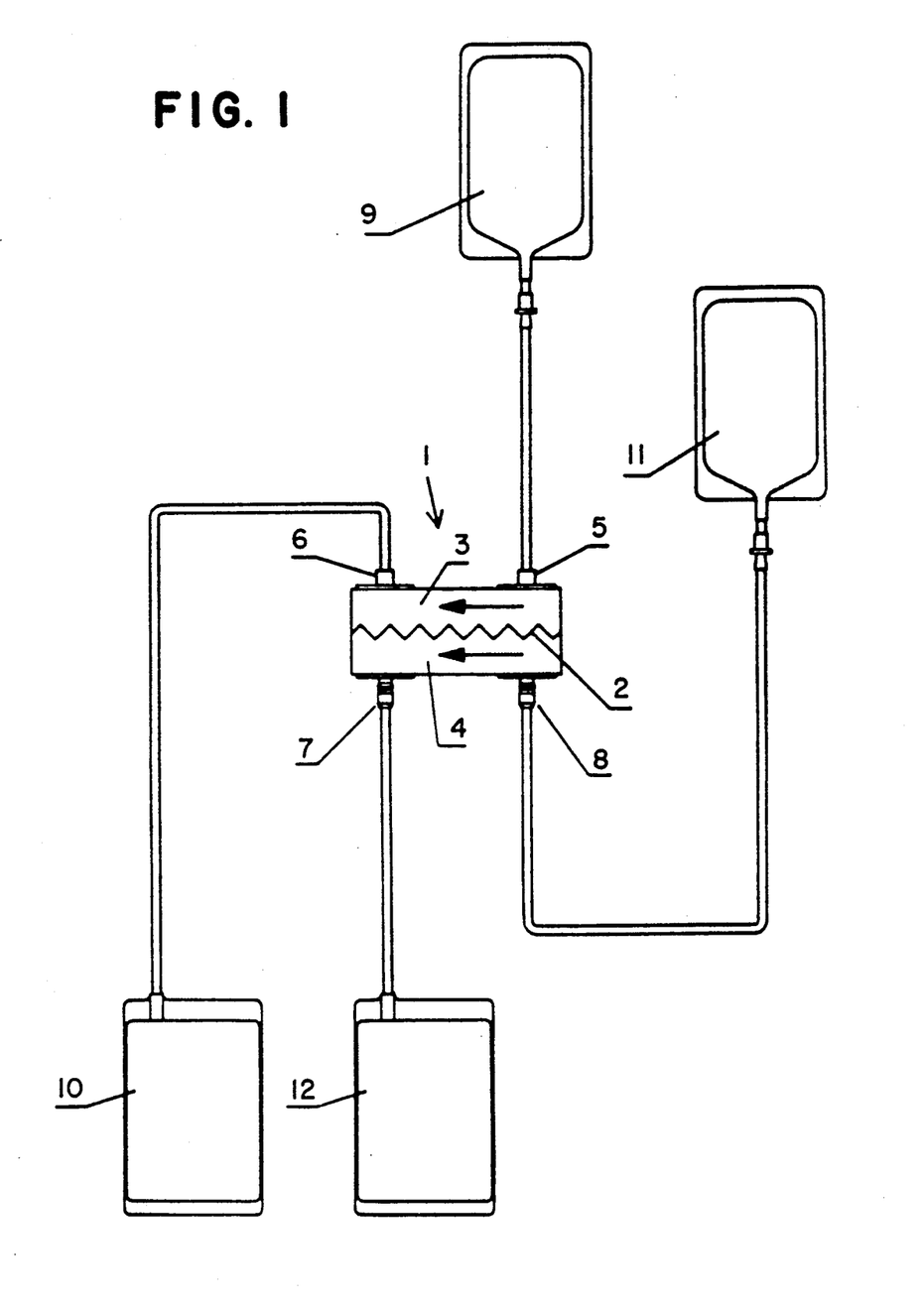
FIG. 1 schematically illustrates a first embodiment of an apparatus incorporating the teachings of the present invention.

With reference to FIG. 1, an exchanger 1 includes a semi-permeable membrane 2 separating the exchanger into first and second compartments 3 and 4, respectively. First compartment 3 is intended for the circulation of blood to be treated, and second compartment 4 is intended for the circulation of a purifying liquid generally prepared by a dialysis liquid generator (not shown). Exchanger 1 is, for example, a hemodialyzer or hemodiafilter.

First compartment (blood compartment) 3 includes an opening 5 intended for the intake of blood to be treated, and an opening 6 intended for the outlet of treated blood. Similarly, second compartment (dialysate compartment) 4 includes an opening 8 for the intake of dialysis liquid, and an opening 7 for the outlet of dialysis liquid. These various openings include end fittings such as gaskets and seals of the type typically used in the art. Before the blood to be treated is introduced, blood compartment 3 is rinsed with a sterile physiological solution originating from a storage bag 9.

This sterile solution is preferably a saline solution of human albumins having a concentration that may be in the range of 4 to 10 g/l. This solution can be circulated by gravitational force by arranging the bag 9 at a suitable height. It is, however, preferable to use a pump (not shown) to regulate the circulation rate of the solution. By way of example and not limitation, such a pump may be conveniently disposed in the line connecting bag 9 and opening 5.

After passing into blood compartment 3, the liquid is evacuated through opening 6 and collected in bag 10. Bag 10 is preferably placed at a height below bag 9 so as to allow the liquid to circulate by gravity.

Dialysate compartment 4 is rinsed using a sterile solution flowing from storage bag 11. This sterile solution is preferably a sterile physiological saline solution, such as a 0.9% solution of sodium chloride After passing into compartment 4, the solution is collected in a collecting bag 12 which is preferably disposed at a lower height than storage bag 11 to allow circulation of the solution by gravity. The invention may employ a single collecting bag instead of the two bags 10 and 12. The single bag should have a capacity at least equal to the sum of the capacities of bags 9 and 11.

Sterile solution may also be circulated from bag 11 through the use of a pump. If gravity is used to circulate the solutions through compartments 3 and 4, bags 9 and 11 must be positioned so as to create a greater pressure near the opening 5 than near opening 8. The solutions may be circulated concurrently through each of the compartments to create a substantially constant pressure differential across the entire membrane.

In accordance with the method of the present invention, a protein film is deposited on at least one side of membrane 2. As embodied herein, this step may be accomplished by rinsing the blood compartment with a sterile solution containing human albumins to deposit a protein film on the surface of the membrane facing the blood compartment. The protein film serves as a protective film. The albumin concentration of the solution is chosen depending upon the type of membrane used and its affinity for proteins. At least one monomolecular protein layer must form on the surface of the membrane This protective film produces a substantial improvement in the biocompatibility of the membrane and also serves as a barrier to all impurities that could be present in the dialysate liquid. To promote the formation of this protein film, a pressure differential may be produced across membrane 2. Thus, if the pressure of the liquid in blood compartment 3 is greater than the pressure of the liquid in dialysate compartment 4, the liquid, passing by convection from blood compartment 3 towards dialysate compartment 4, will promote the deposit of proteins on the membrane.

After the blood compartment has been suitably rinsed with albumin solution, opening 5 of blood compartment 3 is connected to a source of blood to be treated, such as the arterial system of a patient. At the same time, opening 6 is connected to a system collecting the treated blood, such as the patient's venous system. It is then possible to adjust the pressure differential across membrane 2 to allow liquid to pass from blood compartment 3 towards the dialysate compartment 4. This liquid is usually called ultrafiltrate. Finally, openings 7 and 8 of dialysate compartment 4 can he respectively connected to a source of the dialysis liquid and to means for evacuating this dialysis liquid. The blood treatment session can then be carried out by adjusting the various parameters in the usual way.

The protein deposit formed on the blood compartment side of the membrane serves to protect the blood in the event of a change in pressure on either side of the membrane. The deposit prevents contaminating substances that may be present in the dialysis liquid from progressing into the blood. Even if the contaminants pass through membrane 2, the protein deposit formed on the blood compartment side of the membrane acts to block the containments from entering blood compartment 3.

In accordance with another embodiment of the present invention, blood compartment 3 can also be rinsed with a sterile physiological saline solution. After the rinsing stage, and before the blood to be treated is circulated, a sterile solution of human albumins is passed into blood compartment 3. The solution must have a concentration sufficient to rapidly form at least one monomolecular layer of protein on membrane 2. For example, a solution with 40 g/l of albumins can be circulated at a flow rate of 100 ml/mn.

If this two-step process is used, it is possible to have a single sterile solution source for rinsing the two compartments instead of the two bags 9 and 11.

In accordance with another embodiment of the present invention, a sterile physiological saline solution is circulated in blood compartment 3 and a sterile albumin solution is circulated in dialysate compartment 4. In this case, the protein deposit is formed on the dialysate side of membrane 2.

A sterile albumin solution can also be circulated through both compartment 3 and 4 of the exchanger. Thus, a protein deposit is formed on each side of the membrane.

According to another embodiment of the present invention, the deposit of a protein layer on the membrane is not obtained from a sterile human albumin solution, but rather directly by means of the proteins present in the blood to be treated. This has the advantage of considerably reducing the cost of the method. In this case, compartments 3 and 4 of the hemodialyzer are concurrently rinsed with a sterile solution coming from either of the two bags 9 and 11 as depicted in FIG. 1, or from a single source.

When the blood compartment has been sufficiently rinsed, (for example after a 10 min circulation of the solution at a flow rate of 200 ml/min), blood intake opening 5 is connected to the source of the blood to be treated which then circulates through blood compartment 3. When all the rinsing solution is flushed from blood compartment 3 by the blood, circulation is interrupted for a moment and blood outlet opening 6 is connected to means for collecting the treated blood (not shown). During this first circulation of the blood through compartment 3, the sterile rinsing solution in dialysate compartment 4 should be maintained but need not circulate.

Low pressure can also be applied in dialysate compartment 4, so as to cause ultrafiltrate to pass from blood compartment 3 towards dialysate compartment 4 by convection.

Thus, during the first stage of blood circulation, the blood proteins are deposited on the membrane and form a protective film. The greater the affinity of the membrane for proteins, the faster the deposit occurs. For example, the AN 69 membrane, marketed by the HOSPAL Company, has a great affinity for proteins. Experiments have shown that a 3 to 5 minutes circulation of blood to be treated at a flow rate of 100 to 200 ml/mn is sufficient to form a protective film.

It has been observed that maintaining the sterile rinsing solution in dialysate compartment 4 makes it possible to overcome the risk of blood contamination due to substances that may be present in the dialysis liquid. The dialysis liquid, which is normally provided by a dialysis liquid generator may diffuse across membrane 2 if the pressure of the liquid in dialysate compartment 4 becomes greater than the pressure in blood compartment 3.

After the first stage of blood circulation has created a sufficient protein deposit, the sterile rinsing solution is replaced in compartment 4 by purifying liquid supplied by the dialysis liquid generator (not shown).

The session is then continued as usual and the various parameters are chosen to obtain the desired treatment of the blood.

Figure 2:
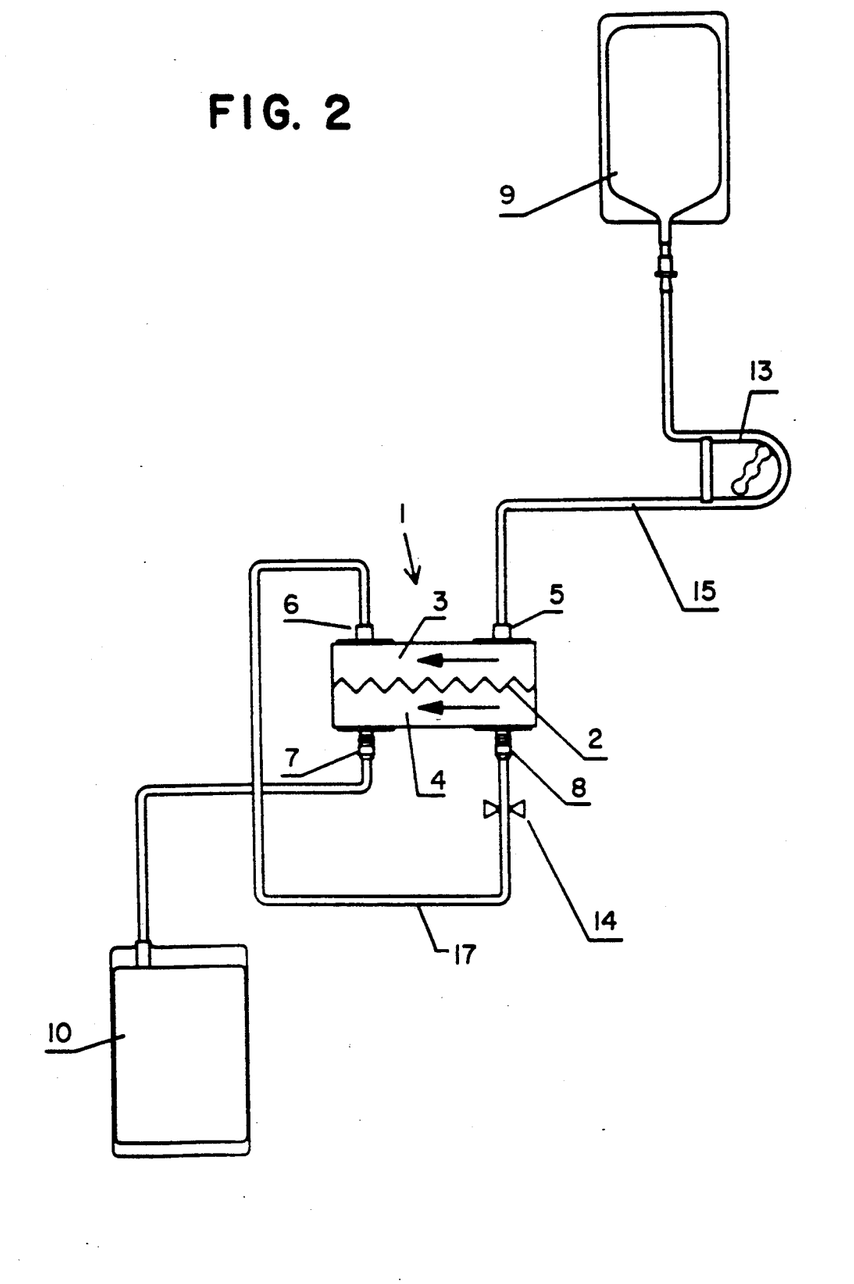
FIG. 2 schematically illustrates a second embodiment of an apparatus incorporating the teachings of the present invention.

The apparatus depicted in FIG. 2 may be used in accordance with this embodiment of the invention. Compartments 3 and 4 of the hemodialyzer 1 are rinsed in series using the same sterile solution coming from storage bag 9. Preferably, a bag of a sterile solution containing 0.9% sodium chloride is used.

This solution is circulated by means of pump 13 which may be the arterial pump of the dialysis apparatus. In a preferred embodiment, pump 13 delivers the solution at a rate of 100 ml/min until compartment 3 is filled. Once compartment 3 is filled, rinsing can continue at a rate of 200 ml/min. The rinsing liquid passes through blood compartment 3, dialysate compartment 4, and is subsequently collected in bag 10. The liquid is concurrently circulated through both compartments so as to maintain a substantially constant pressure differential across the entire membrane 2.

When the bag 9 is empty, pump 13 is stopped, and bag 9 is replaced with a blood source to be treated. This may be achieved by connecting arterial line 15 to the arterial system of a patient.

Pump 13 is then restarted to cause the blood to be treated to circulate at a flow rate of preferably 100 ml/min.

Once blood compartment 3 is filled, outlet opening 6 is connected to means for collecting the treated blood, such as, the venous system of a patient.

With reference to FIG. 2, as blood is circulated through blood compartment 3, the circulation of sterile solution inside dialysate compartment 4 is stopped by means of an obturation device such as clamp 14.

The blood to be treated is then circulated inside the hemodialyzer for 3 to 5 min to allow the formation of a protein deposit on membrane 2 sufficient to constitute a protective film. After this circulation stage, collecting bag 10 is replaced by a dialysis liquid source and opening 8 is connected to means for evacuating the used dialysis liquid. The blood treatment session then continues in the usual manner.

Tests were carried out on patients usually exhibiting hypersensitive anaphylactic reactions. When the rinsing and priming method of the present invention was implemented, no reaction of this type was observed.

Instead of using a sterile solution containing only 0.9% sodium chloride, it is particularly advantageous to use a rinsing saline liquid preferably containing 2000 IU/l of heparin.

By using such a solution, the membrane becomes impregnated with heparin during the rinsing procedure. This reduces coagulation problems that can occur during the first minutes of extracorporeal circulation if anti-coagulation procedures are not properly followed.

As blood enters exchanger 1, it contacts the heparin impregnated membrane 2. This, in combination with a heparinized liquid in dialysate compartment 4, reduces the possibility of coagulation.

Figure 3:
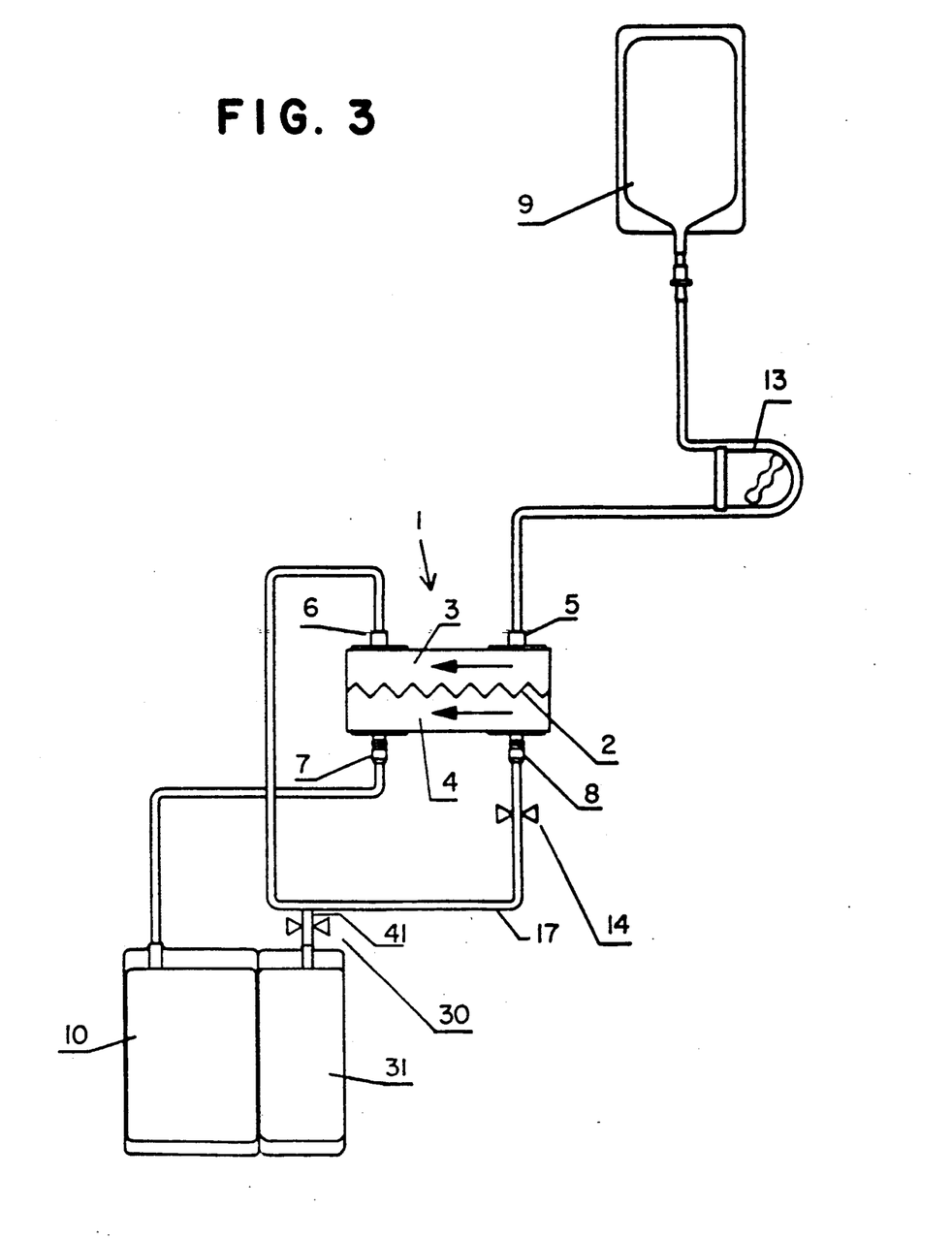
FIG. 3 schematically illustrates a third embodiment of an apparatus incorporating the teachings of the present invention.

It is possible to further improve the quality of rinsing using the apparatus depicted in FIG. 3. In fact, it has been discovered that most of the manufacturing and sterilization residues are eliminated during the first stage of the rinsing procedure, i.e. the first 500 ml of rinsing liquid. Thus, it is advantageous not to use this first amount of rinsing liquid coming from the blood compartment 3 to rinse the dialysate compartment 4.

Therefore, during the first stage it is advantageous to open clamp 30 and close clamp 14. This causes the first part of the rinsing liquid to be diverted to bag 31. When bag 31 is filled, pump 13 is momentarily stopped to allow clamp 30 to be closed and clamp 14 to be opened.

During the second stage, pump 13 is restarted so that the second part of the rinsing liquid can circulate through blood compartment 3 and then through dialysate compartment 4, as already described in connection with FIG. 2. Clamps 30 and 14 can be replaced by any equivalent means, such as a 3-way valve.

In accordance with the invention, the apparatus includes first conduit means for connecting a source of sterile physiological saline solution to the first compartment. As embodied herein and depicted in FIG. 5, the first conduit means includes arterial line 15 connecting bag 9 with first compartment 3.

Figure 5:
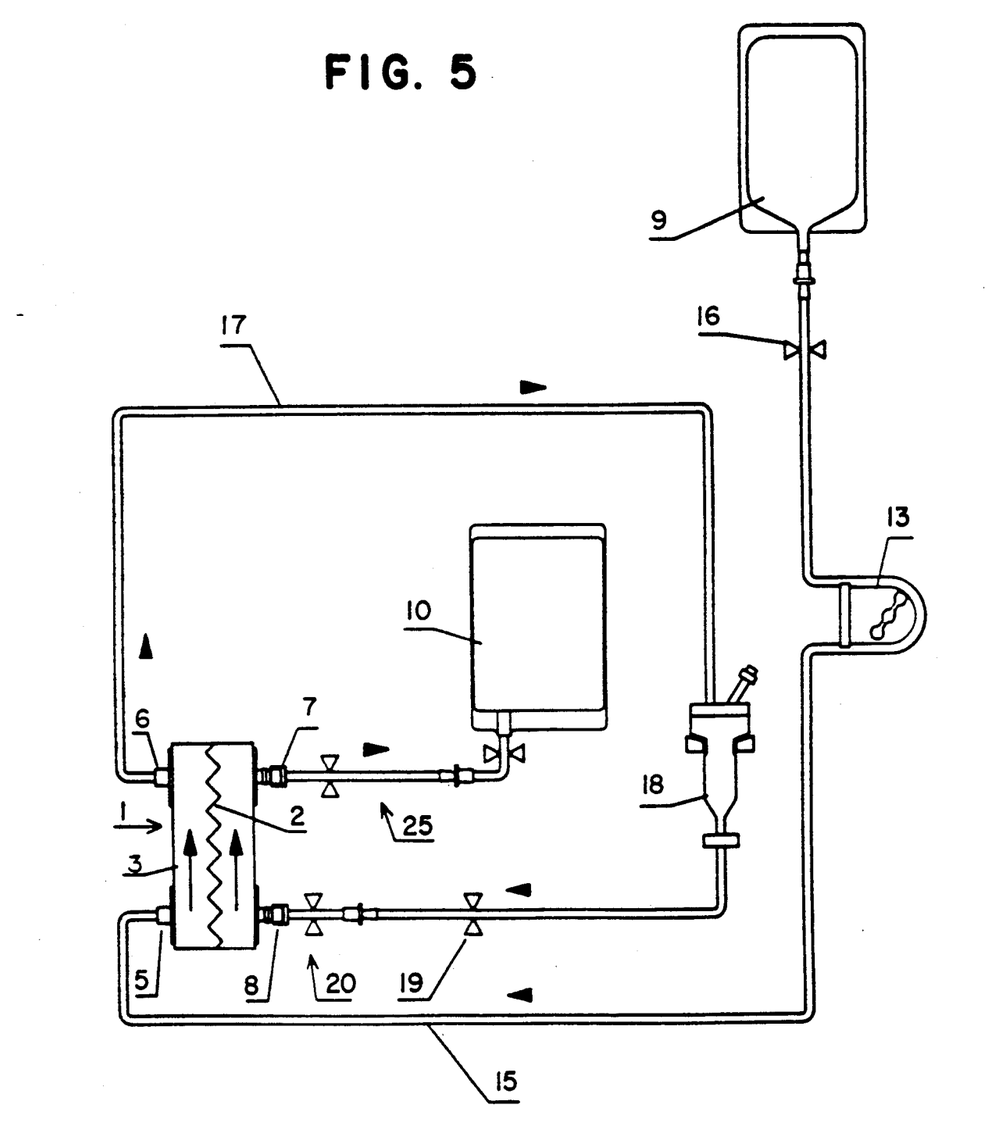
FIG. 5 schematically illustrates a fifth embodiment of an apparatus incorporating the teachings of the present invention.

Also, in accordance with the present invention the apparatus includes second conduit means for connecting the first compartment to the second compartment. As embodied herein, the second conduit means includes second conduit 17, outlet opening 6, and outlet opening 8. Second conduit 17 connects outlet 6 of the first compartment with outlet 8 of the second compartment.

Figure 4:
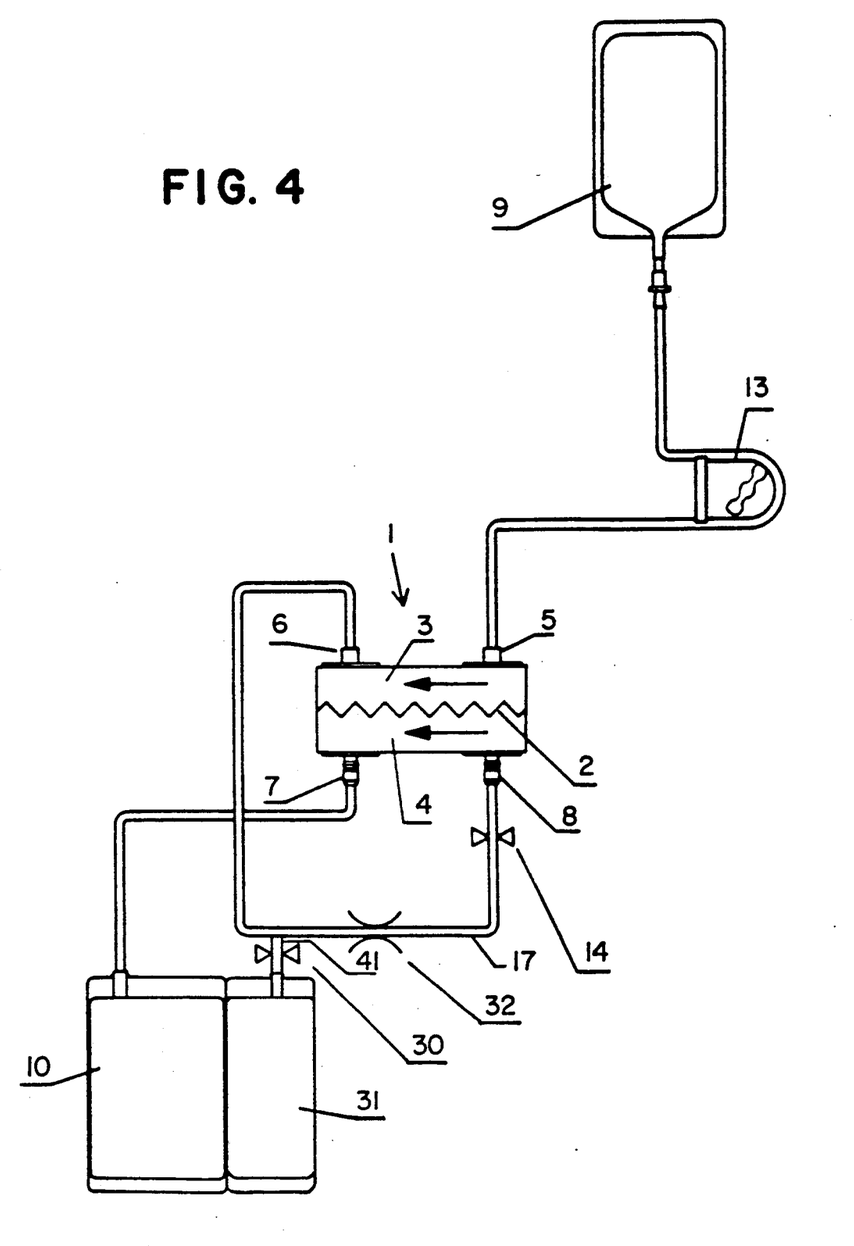
FIG. 4 schematically illustrates a fourth embodiment of an apparatus incorporating the teachings of the present invention.

The apparatus of the present invention also includes third conduit means comprised of conduit 41 for connecting outlet opening 6 and second conduit 17 with bag 31, and means for diverting a predetermined amount of solution from conduit 17 to bag 31 prior to entering second compartment 4. In accordance with a preferred embodiment and as depicted in FIG. 4, the diverting means includes an obturation means comprised of clamps 30 and 14 and flow restrictor 32.

During the first stage of the rinsing process, clamp 30 is opened and flow restrictor 32 is provided on second conduit 17 downstream from the junction with the bag 31. This flow restrictor creates a preferred path for liquid coming from compartment 3 to collecting bag 31. When collecting bag 31 is filled, pressure increases in connecting line 41 and upon reaching a predetermined or selected pressure in conduit 41, the flow restrictor opens and the rinsing liquid then flows through flow restrictor 32, dialysate compartment 4, and is collected in bag 10. For safety reasons, clamp 30 is closed when bag 31 has been filled.

The use of the flow restrictor 32 advantageously increases the pressure differential between compartments 3 and 4, thus increasing the convective flow from compartment 3 to compartment 4 across membrane 2. The increase in convective flow reduces diffusion of undesirable particles from compartment 4 to compartment 3.

In accordance with a further embodiment of the present invention, as depicted in FIG. 3, diverting means includes bag 31, third conduit 41, and obturation means such as clamps 30 and 14. As described earlier, during the first stage of the rinsing procedure, clamp 30 on third conduit 41 is opened and clamp 14 is closed. This causes the first part of the liquid to be diverted to bag 31. When bag 31 is filled, pump 13 is momentarily stopped to allow clamp 30 to be closed and clamp 14 to be opened. Thus, the embodiment of the present invention illustrated in FIG. 3 precludes the need for use of flow restrictor 32.

To implement the method of rinsing and priming described above, the present invention may include an apparatus such as depicted in FIG. 5. The apparatus of FIG. 5 includes first conduit means comprised of arterial line 15 connecting the blood intake opening 5 to storage bag 9. Arterial line 15 includes an obturation device 16, between pump 13 and storage bag 9.

Figure 6:
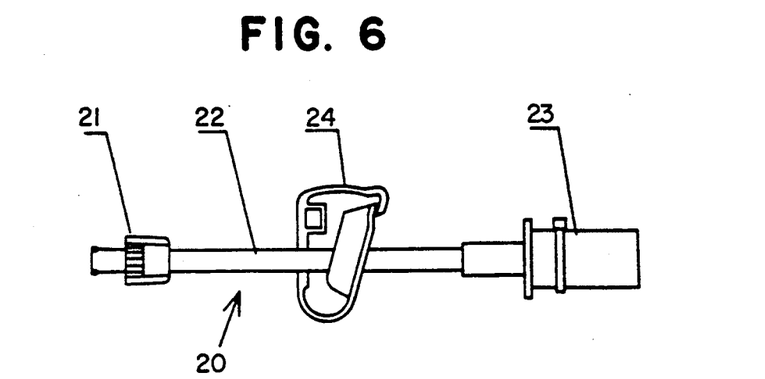
FIG. 6 illustrates the first connection section of FIG. 5.
Figure 7:
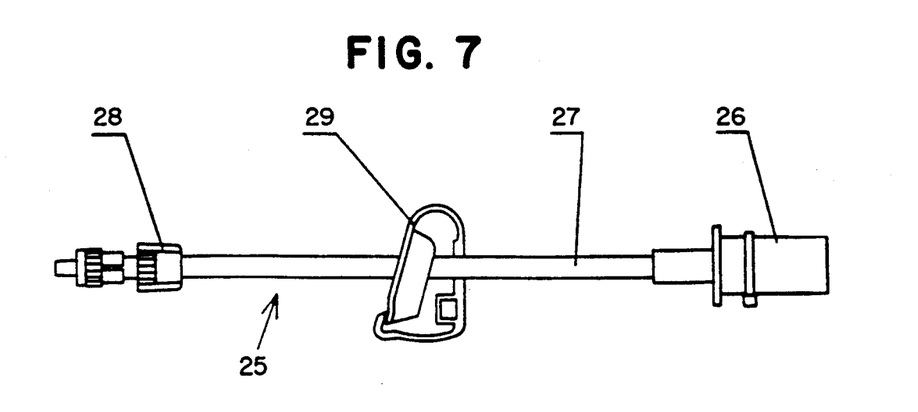
FIG. 7 illustrates the second connecting line of FIG. 5.

The apparatus also includes second conduit means for connecting blood inlet opening 6 and inlet opening 8. As embodied herein, the second conduit means comprises second conduit 17 passing through bubble trap 18 and having an obturation device such as a clamp 19 at one end, as well as a first connecting section 20 between the end of second conduit line 17 and opening 8. The first connecting section 20 is shown in greater detail in FIG. 6 and comprises a connector 21 such as a female Luer-Lock that connects the end of second conduit 17 to line 22. Line 22 is preferably made of polyvinyl chloride and has a Hansen type connector 23 at its other end disposed to be connected to dialysate opening 8. Line 22 also includes an obturation device 24 such as a clamp. As depicted in FIG. 5, second connecting line 25 connects opening 7 of dialysate compartment 4 to collecting bag 10. Second connecting line 25, shown in detail in FIG. 7, comprises connector 26 disposed at one end of line 27 for connection to opening 7 of dialysate compartment 4. Line 27 is preferably made of polyvinyl chloride and also includes a male Luer-Lock type connector 28 disposed at its opposite end to be connected to the corresponding female Luer type connector of storage bag 10. Line 27 further comprises an obturation device 29 such as a clamp.

Figure 8:
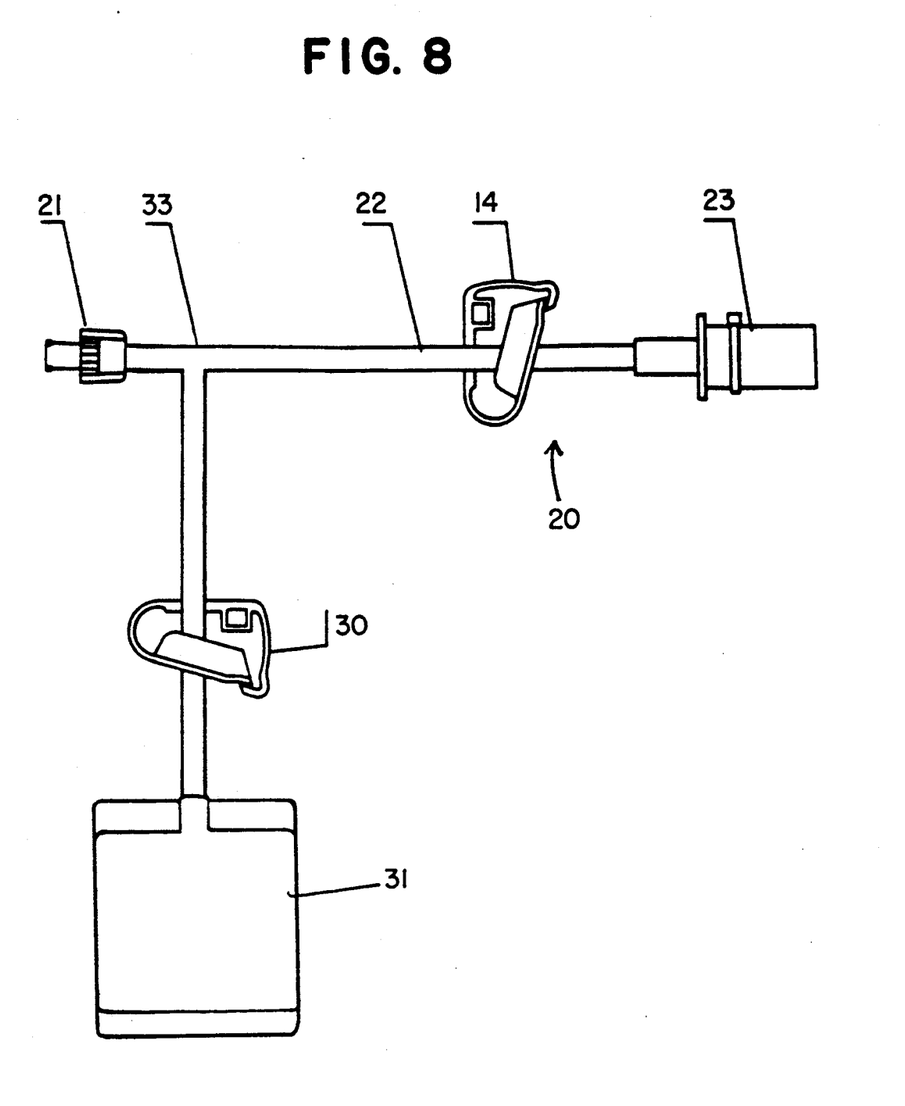
FIG. 8 illustrates an embodiment of the diversion means of FIG. 3.

In order to implement the embodiment of the invention illustrated in FIG. 5, connection section 20 is provided, as depicted in FIG. 8. Connecting section 20 includes T-portion 33 that enables the rinsing liquid to flow either into the collection bag 31 when clamp 30 is opened and clamp 14 closed, or into compartment 4 when clamp 30 is closed and clamp 14 opened.

Figure 9:
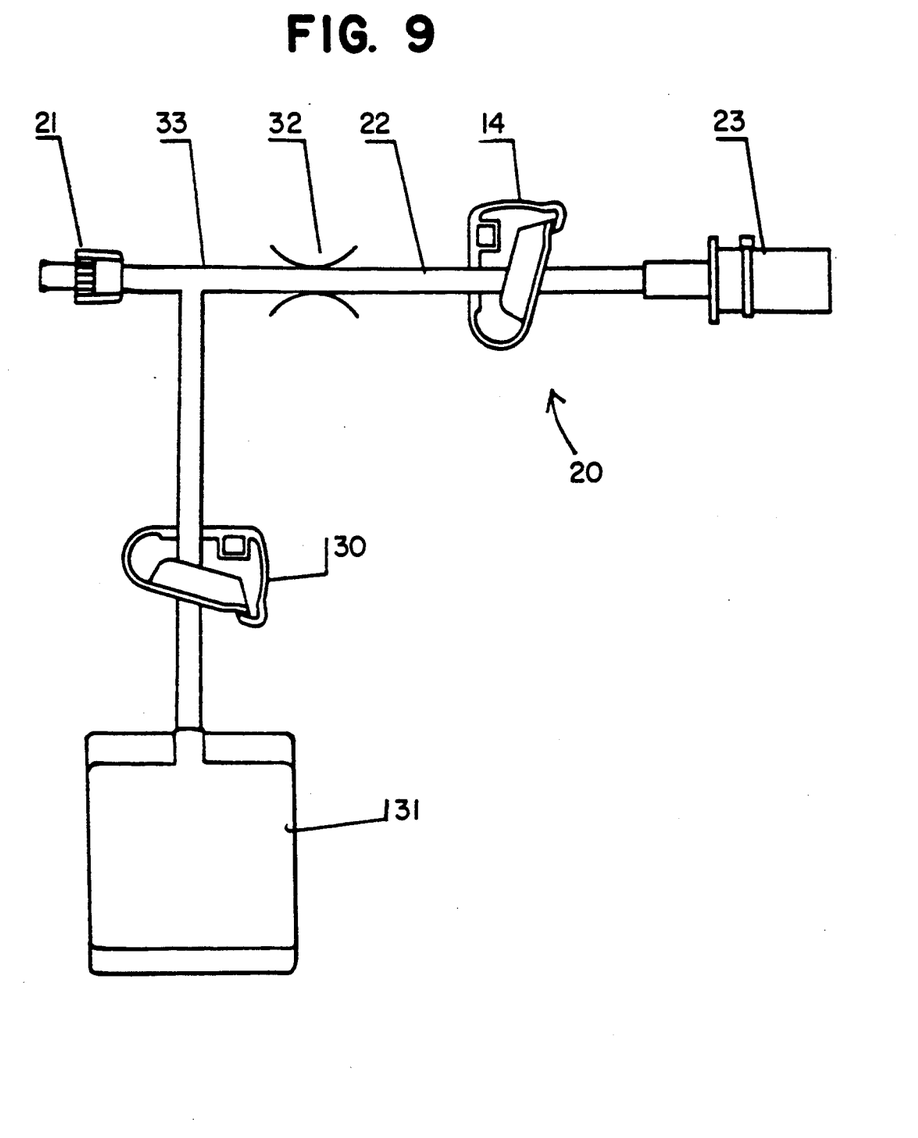
FIG. 9 illustrates an embodiment of the diversion means of FIG. 4.

Implementation of the invention described in connection with FIG. 4 can be simplified by modifying connecting section 20 as depicted in FIG. 9. This modification essentially includes adding flow restrictor 32 downstream of Hansen connector 23 and upstream of T-portion 33. This flow restrictor 32 can be a tube with a portion having a reduced internal diameter.

Collecting bag 31 may be an independent bag having a volume equal to the volume of the first part of the rinsing liquid to be disposed of after its passage through blood compartment 3.

Bags 10 and 31 can also be combined to form a single bag having two complementary chambers. The total volume of the two complimentary chambers should be greater than or equal to the volume of bag 9.

The rinsing and priming method according to the present invention is very simple for hospital staff to implement, because it is not necessary with this method to change the position of the exchanger during the procedure as was necessary in the prior art.

In the present invention, the exchanger can be rinsed and primed without introducing any air bubbles. The two compartments are filled from the bottom to the top to minimize the introduction of air bubbles without having to manipulate the exchanger.

Moreover, since liquid flows through compartments concurrently, convective flow from blood compartment 3 towards the dialysate compartment 4 assures that there is no retrofiltration.

The method according to the present invention can be applied irrespective of the structure of the membrane used (planar, with hollow fibers, tubular, flattened) and irrespective of the membrane's chemical make-up. However, membranes having a strong affinity for proteins, such as polyacrylonitrile based membranes, are particularly suitable for this method.

What is claimed is:

1. A method for rinsing and priming an exchanger divided into first and second compartments by a semi-permeable membrane, the first compartment intended for circulating blood to be treated and the second compartment intended for circulating a purifying liquid, comprising the steps of:
   (a) circulating a sterile solution through the first compartment to rinse the same;
   (b) circulating a sterile solution through the second compartment to rinse the same; and
   (c) depositing a protein film on at least one side of the semi-permeable membrane by circulating a sterile albumin solution through the first compartment.

2. The method of claim 1 wherein the step of depositing protein film includes circulating a sterile albumin solution through both the first and second compartments to deposit a protein film on both sides of the membrane.

3. The method of claim 1, wherein step (c) includes the sub-step of:
   (a) circulating blood to be treated through the first compartment, after rinsing the first compartment with the sterile solution, to deposit the protein film on the membrane, while maintaining the sterile rinsing solution in the second compartment.

4. The method of claim 1, wherein sterile solution is concurrently circulated through the first and second compartments and wherein step c includes the sub-step of circulating blood to be treated through the first compartment to deposit a protein film on the membrane while maintaining the sterile rinsing solution in the second compartment after rinsing the first and second compartments.

5. The method of claim 1, wherein the sterile solutions are circulated through the first and second compartments in the same direction.

6. An apparatus for rinsing and priming an exchanger, the exchanger having a first end and a second end and divided into first and second compartments by a semi-permeable membrane, the first compartment intended for circulating blood to be treated and the second compartment intended for circulating a purifying liquid, comprising:
   a source of sterile physiological saline solution;
   means for collecting said saline solution;
   an intake opening and an outlet opening formed in said first compartment;
   an intake opening and an outlet opening formed in said second compartment;
   first conduit means for flow communicating said intake opening of said first compartment to said source of sterile solution;
   second conduit means for flow communicating said outlet opening of said first compartment to said outlet opening of said second compartment;
   third conduit means for evacuating a portion of the sterile solution flowing through said second conduit means from said second conduit means to said collecting means; and
   fourth conduit means for flow communicating said inlet opening of said second compartment with said collecting means.

7. The apparatus of claim 6, wherein the third conduit means includes obturation means for selectively passing said solution into the second compartment upon sensing a predetermined pressure in said second conduit means.

8. The apparatus of claim 6, wherein the collecting means includes a first receptacle for connection to said third conduit means and a second receptacle for connection to said fourth conduit means.

9. The apparatus of claim 6, wherein said first conduit means is connected to said first compartment proximate the first end of the apparatus and said second conduit means is connected to said second compartment proximate the first end of the apparatus.

10. The apparatus of claim 6, wherein said second conduit means is connected between said first and second compartments to direct fluid flow through said second compartment in substantially the same direction as fluid flow through said first compartment.

11. An apparatus for rinsing and priming an exchanger, the exchanger having a first end and a second end and divided into first and second compartments by a semi-permeable membrane, the first compartment intended for circulating blood to be treated and the second compartment intended for circulating a purifying liquid, comprising:
   a source of sterile physiological saline solution;
   means for collecting said saline solution;
   first and second openings formed in said first compartment;
   first and second openings formed in said second compartment;
   first conduit means for flow communicating said first opening of said first compartment to said source of sterile solution;
   second conduit means for flow communicating said second opening of said first compartment to said first opening of said second compartment;
   third conduit means for evacuating a portion of the sterile solution flowing through said second conduit means from said second conduit means to said collecting means; and
   fourth conduit means for flow communicating said second opening of said second compartment with said collecting means.

12. The apparatus of claim 11, wherein said second conduit means is connected between said first and second compartments to direct fluid flow through said second compartment in substantially the same direction as fluid flow through said first compartment.

13. A method for rinsing and priming an exchanger divided into first and second compartments by a semi-permeable membrane, the first compartment intended for circulating blood to be treated and the second compartment intended for circulating a purifying liquid, comprising the steps of:
   (a) circulating a sterile solution through the first compartment to rinse the same;
   (b) circulating a sterile solution through the second compartment to rinse the same; and
   (c) depositing a protein film on at least one side of the semi-permeable membrane by circulating a sterile albumin solution through the second compartment.

14. A method for rinsing and priming an exchanger divided into first and second compartments by a semi-permeable membrane, the first compartment intended for circulating blood to be treated and the second compartment intended for circulating a purifying liquid, comprising the steps of:
   (a) circulating a sterile solution through the first compartment to rinse the same;
   (b) circulating a sterile solution through the second compartment to rinse the same; and (c) circulating blood to be treated through the first compartment to deposit a protein film on the membrane while maintaining the sterile solution in the second compartment after rinsing the first compartment with the sterile solution.

15. The method of claim 14, wherein the sterile solution circulating through the first and second compartments originates from the same source.

16. A method according to claim 14, wherein the sterile solutions are heparinized physiological saline solutions.

17. A method for rinsing and priming an exchanger divided into first and second compartments by a semipermeable membrane, the first compartment intended for circulating blood to be treated and the second compartment intended for circulating a purifying liquid, comprising the steps of:
   (a) circulating a sterile solution through the first compartment to rinse the same;
   (b) concurrently circulating a sterile solution through the second compartment to rinse the same; and
   (c) circulating blood to be treated through the first compartment to deposit a protein film on the membrane while maintaining the sterile solution in the second compartment after rinsing the first and second compartments.

18. The method of claim 17, wherein sterile solution exiting the first compartment is directed through the second compartment.

19. The method of claim 17, wherein the step of circulating sterile liquid through the second compartment includes the substep of:
   (a) directing the sterile solution exiting the first compartment into and through the second compartment;
   (b) draining off a predetermined amount of the sterile solution prior to entering the second compartment and after exiting the first compartment.

20. The method according to claim 19, wherein the predetermined amount of sterile solution drained off comprises a first portion of sterile solution exiting the first compartment, said first portion being about 500 ml.

* * * * *